(12) United States Patent
Hon (10) Patent No.: US 9,326,549 B2
(45) Date of Patent: *May 3, 2016

(54) ELECTRONIC CIGARETTE

(71) Applicant: FONTEM HOLDINGS 1 B.V., Amsterdam (NL)

(72) Inventor: Lik Hon, North Point (HK)

(73) Assignee: Fontem Holdings 1 B.V., Amsterdam (NL)

( * ) Notice: Subject to any disclaimer, the term of this patent is extended or adjusted under 35 U.S.C. 154(b) by 0 days.

This patent is subject to a terminal disclaimer.

(21) Appl. No.: 14/719,061

(22) Filed: May 21, 2015

(65) Prior Publication Data
US 2015/0250229 A1    Sep. 10, 2015

Related U.S. Application Data

(60) Continuation of application No. 14/525,066, filed on Oct. 27, 2014, which is a continuation of application No. 13/777,927, filed on Feb. 26, 2013, now Pat. No. 8,893,726, which is a division of application No.

(Continued)

(30) Foreign Application Priority Data

Apr. 14, 2004    (CN) .............................. 2004 0 031182

(51) Int. Cl.
| | |
|---|---|
| *A24F 47/00* | (2006.01) |
| *A61M 15/00* | (2006.01) |
| *A61M 15/06* | (2006.01) |
| *F24H 3/00* | (2006.01) |
| *H05B 1/02* | (2006.01) |
| *H05B 3/00* | (2006.01) |

(52) U.S. Cl.
CPC ............. *A24F 47/008* (2013.01); *A24F 47/002* (2013.01); *A61M 15/0085* (2013.01); *A61M 15/06* (2013.01); *F24H 3/002* (2013.01); *H05B 1/0291* (2013.01); *H05B 3/0004* (2013.01)

(58) Field of Classification Search
CPC .... A24F 47/008; A24F 47/004; A24F 47/002
USPC .............................. 131/270, 273; 128/202.21
See application file for complete search history.

(56) References Cited

U.S. PATENT DOCUMENTS

| | | | |
|---|---|---|---|
| 705,919 A | 7/1902 | Gill | |
| 1,775,947 A * | 9/1930 | Robinson | ................. 128/203.27 |

(Continued)

FOREIGN PATENT DOCUMENTS

| | | |
|---|---|---|
| AU | 2004234199 | 11/2004 |
| CN | 1135860 A | 11/1996 |

(Continued)

OTHER PUBLICATIONS

Andrus, Paul G. et al., Nicotine Microaerosol Inhaler, Canadian Respiratory Journal (1999) 6(6) p. 509-512.

(Continued)

*Primary Examiner* — Michael H Wilson
*Assistant Examiner* — Dionne Walls Mayes
(74) *Attorney, Agent, or Firm* — Perkins Coie LLP (57) ABSTRACT

An electronic cigarette includes a shell and a mouthpiece. The external wall of the shell has an air inlet. An atomizer and a liquid-supply are in contact with each other. The air inlet, atomizer, and an aerosol passage are interconnected.

27 Claims, 5 Drawing Sheets

Related U.S. Application Data

13/560,789, filed on Jul. 27, 2012, now Pat. No. 8,490,628, which is a continuation of application No. 12/944,123, filed on Nov. 11, 2010, now Pat. No. 8,393,331, which is a continuation of application No. 10/587,707, filed as application No. PCT/CN2005/000337 on Mar. 18, 2005, now Pat. No. 7,832,410.

(56) References Cited

U.S. PATENT DOCUMENTS

| | | | |
|---|---|---|---|
| 2,057,353 A * | 10/1936 | Whittemore, Jr. | 392/395 |
| 2,631,219 A | 3/1953 | Suchy | |
| 3,060,429 A | 10/1962 | Winston | |
| 3,200,819 A | 8/1965 | Gilbert | |
| 3,203,025 A | 8/1965 | Shreur | |
| 3,400,998 A | 9/1968 | Daugherty | |
| 3,431,393 A | 3/1969 | Katsuda | |
| 3,479,561 A | 11/1969 | Janning | |
| 3,502,588 A | 3/1970 | Winberg | |
| 3,747,120 A | 7/1973 | Stemme | |
| 3,952,798 A | 4/1976 | Jacobson | |
| 4,171,000 A | 10/1979 | Uhle | |
| 4,303,083 A | 12/1981 | Burruss | |
| 4,641,053 A | 2/1987 | Takeda | |
| 4,676,237 A | 6/1987 | Wood | |
| 4,735,217 A | 4/1988 | Gerth | |
| 4,756,318 A | 7/1988 | Clearman | |
| 4,771,295 A | 9/1988 | Baker | |
| 4,771,796 A * | 9/1988 | Myer | 131/273 |
| 4,797,692 A | 1/1989 | Ims | |
| 4,848,374 A | 7/1989 | Chard | |
| 4,945,448 A | 7/1990 | Brememour | |
| 4,945,929 A * | 8/1990 | Egilmex | 131/273 |
| 4,945,931 A | 8/1990 | Gori | |
| 4,947,874 A | 8/1990 | Brooks | |
| 4,947,875 A * | 8/1990 | Brooks et al. | 131/330 |
| 4,972,855 A | 11/1990 | Kuriyama | |
| 4,990,939 A | 2/1991 | Sekiya | |
| 5,042,470 A | 8/1991 | Kanesaka | |
| 5,060,671 A | 10/1991 | Counts | |
| 5,095,921 A | 3/1992 | Losee | |
| 5,124,200 A | 6/1992 | Mallonee | |
| 5,144,962 A | 9/1992 | Counts | |
| 5,159,940 A | 11/1992 | Hayward et al. | |
| 5,179,966 A | 1/1993 | Losee | |
| 5,224,265 A | 7/1993 | Dux | |
| 5,249,586 A | 10/1993 | Morgan | |
| 5,261,424 A | 11/1993 | Sprinkel | |
| 5,322,075 A | 6/1994 | Deevi | |
| 5,327,915 A | 7/1994 | Porenski | |
| 5,438,978 A | 8/1995 | Hardester | |
| 5,497,791 A | 3/1996 | Bowen | |
| 5,505,214 A | 4/1996 | Collins | |
| 5,591,368 A | 1/1997 | Fleischhauer | |
| 5,646,666 A | 7/1997 | Cowger | |
| 5,666,977 A | 9/1997 | Higgins | |
| 5,666,978 A | 9/1997 | Counts | |
| 5,703,633 A | 12/1997 | Gehrer | |
| 5,730,158 A | 3/1998 | Collins | |
| 5,743,251 A | 4/1998 | Howell | |
| 5,745,985 A | 5/1998 | Ghosh | |
| 5,799,663 A | 9/1998 | Gross | |
| 5,816,263 A | 10/1998 | Counts | |
| 5,819,756 A | 10/1998 | Mielordt | |
| 5,894,841 A | 4/1999 | Voges | |
| 5,996,589 A | 12/1999 | St. Charles | |
| 6,040,560 A | 3/2000 | Fleischhauer | |
| 6,062,213 A | 5/2000 | Fuisz | |
| 6,102,036 A | 8/2000 | Slutsky | |
| 6,155,268 A | 12/2000 | Takeuchi | |
| 6,196,218 B1 | 3/2001 | Voges | |
| 6,234,167 B1 | 5/2001 | Cox | |
| 6,322,268 B1 | 11/2001 | Kaufmann | |
| 6,354,293 B1 | 3/2002 | Madison | |
| 6,357,671 B1 | 3/2002 | Cewers | |
| 6,443,146 B1 | 9/2002 | Voges | |
| 6,471,782 B1 | 10/2002 | Fang | |
| 6,501,052 B2 | 12/2002 | Cox | |
| 6,598,607 B2 | 7/2003 | Adiga | |
| 6,620,659 B2 | 9/2003 | Emmma | |
| 6,701,921 B2 | 3/2004 | Sprinkel | |
| 6,722,763 B1 | 4/2004 | Hsu | |
| 6,810,883 B2 | 11/2004 | Felter | |
| 6,854,461 B2 | 2/2005 | Nichols | |
| 6,854,470 B1 | 2/2005 | Pu | |
| 7,059,307 B2 | 6/2006 | Pellizari | |
| 7,100,618 B2 | 9/2006 | Dominguez | |
| 7,131,599 B2 | 11/2006 | Katase | |
| 7,143,766 B2 | 12/2006 | Schuster | |
| 7,284,424 B2 | 10/2007 | Kanke | |
| 7,832,410 B2 | 11/2010 | Hon | |
| 7,883,031 B2 | 2/2011 | Collins | |
| 7,997,280 B2 | 8/2011 | Rosenthal | |
| 8,156,944 B2 | 4/2012 | Han | |
| 8,511,318 B2 | 8/2013 | Hon | |
| 2001/0026788 A1 | 10/2001 | Piskorz | |
| 2003/0108342 A1 | 6/2003 | Sherwood | |
| 2003/0150446 A1 | 8/2003 | Patel | |
| 2005/0016550 A1 | 1/2005 | Katase | |
| 2006/0016453 A1 | 1/2006 | Kim | |
| 2006/0093977 A1 | 5/2006 | Pellizari | |
| 2006/0196518 A1 | 9/2006 | Hon | |
| 2007/0125765 A1 | 6/2007 | Nelson | |

FOREIGN PATENT DOCUMENTS

| | | |
|---|---|---|
| CN | 1233436 | 11/1999 |
| CN | 1252961 A | 5/2000 |
| CN | 03111582.9 | 4/2003 |
| CN | 200410048792.6 | 6/2004 |
| CN | 1530041 A | 9/2004 |
| CN | 1541577 A | 11/2004 |
| CN | 1575673 A | 2/2005 |
| CN | 2719043 | 8/2005 |
| CN | 1284493 C | 11/2006 |
| CN | 201020546169.4 | 9/2010 |
| CN | 201120050555.9 | 2/2011 |
| CN | 201120066344.4 | 3/2011 |
| CN | 201797997 U | 4/2011 |
| CN | 202026802 U | 11/2011 |
| CN | 202026804 U | 11/2011 |
| EP | 0230420 | 8/1987 |
| EP | 0295122 | 12/1988 |
| EP | 0342538 A | 11/1989 |
| EP | 0358002 | 3/1990 |
| EP | 0358114 A2 | 3/1990 |
| EP | 0488488 B1 | 3/1992 |
| EP | 0545186 A2 | 6/1993 |
| EP | 0619761 A1 | 10/1994 |
| EP | 0430566 B1 | 4/1995 |
| EP | 0703735 | 4/1996 |
| EP | 0845220 A1 | 6/1998 |
| EP | 0951219 | 11/2002 |
| EP | 0845220 B1 | 9/2003 |
| EP | 1736065 A1 | 12/2006 |
| WO | WO8602528 A2 | 5/1986 |
| WO | WO9409842 | 5/1994 |
| WO | WO9421317 | 9/1994 |
| WO | WO9740876 | 11/1997 |
| WO | WO9817130 | 4/1998 |
| WO | WO9817131 A1 | 4/1998 |
| WO | WO0105459 | 1/2001 |
| WO | WO0132247 A1 | 5/2001 |
| WO | WO0133247 A1 | 5/2001 |
| WO | WO02098390 A2 | 12/2002 |
| WO | WO03000324 A1 | 1/2003 |
| WO | WO03055486 | 7/2003 |
| WO | WO03101454 | 12/2003 |
| WO | WO2004023222 | 3/2004 |
| WO | WO2004080216 | 3/2004 |

(56) References Cited

FOREIGN PATENT DOCUMENTS

| | | |
|---|---|---|
| WO | WO2004043175 A1 | 5/2004 |
| WO | WO2004095955 | 11/2004 |

OTHER PUBLICATIONS

CN Creative and Intellicig USA, CV11-6268 Invalidity Contentions, Apr. 12, 2012.
Collins, John M., Expert Report—Invalidity (Excerpts), CV14-01645, Jun. 18, 2015.
Collins, John M., Expert Report—Invalidity, CV14-01645—Appendix G-'331, Jun. 18, 2015.
Collins, John M., Expert Report—Invalidity, CV14-01645—Appendix H-'628, Jun. 18, 2015.
Collins, John M., Expert Report—Invalidity, CV14-01645—Appendix K-1-'726, Jun. 18, 2015.
Collins, John M., Expert Report—Invalidity, CV14-01645—Appendix K-2-'726, Jun. 18, 2015.
Collins, John M., Expert Report—Invalidity, CV14-01645—Appendix K-3-'726, Jun. 18, 2015.
Collins, John M., Expert Report—Invalidity, CV14-01645—Appendix K-4-'726, Jun. 18, 2015.
Collins, John M., Expert Report—Invalidity, CV14-01645—Appendix K-5-726, Jun. 18, 2015.
Collins, John M., Expert Report—Invalidity, CV14-01645—Appendix K-6-'726, Jun. 18, 2015.
Cyphert Gil DBA NU1S, CV11-0367 Invalidity Contentions, Apr. 12, 2012.
European Patent Office, Supplemental European Search Report for EP05729107, Jul. 31, 2007.
European Patent Office, Supplemental Partial European Search Reports for EP05729107, May 22, 2007.
Hewlett-Packard, Thermal Ink—Jet Print Cartridge Designers Guide (2nd Edition), Jan. 12, 1995.
Introduction to selecting and using electronic components, ISBN7-111-13752-3.
IP Australia, Examiners Report for AU 2005232354, Jan. 12, 2010.
IP Australia, Search and Examination Report for SG200604498-6, Apr. 16, 2008.
Manual for Electric Engineers, 2nd Ed, Mar. 2000.
Manual for Mechanical Designers, 4th Ed, Jan. 2002.
Materials Manual—Nonmetal, Jul. 1, 1985.
NJOY, Inc. et al, Defendants' Joint Invalidity Contentions, CV14-01645 etc., Aug. 7, 2014 (see pp. 7-16).
NJOY, Inc. et al., Defendants' Joint Invalidity Contentions, CV-14-01645 etc., Attachment B—Claim Charts for Patent 8393331, Aug. 7, 2014.
NJOY, Inc. et al., Defendants' Joint Invalidity Contentions, CV-14-01645 etc., Attachment C—Claim Charts for Patent 8490628, Aug. 7, 2014.
NJOY, Inc. et al, Defendants' Joint Invalidity Contentions, CV14-01645 etc., Feb. 26, 2015 (see pp. 7-12).
NJOY, Inc. et al., Defendant's Joint Invalidity Contentions, CV14-01645 etc., Exhibit B—Claim Charts for Patent 8893726—Feb. 26, 2015.
NJOY, Inc., Petition for Inter Partes Review of U.S. Pat. No. 8393331—IPR2014-01289, Aug. 14, 2014.
NJOY, Inc., Petition for Inter Partes Review of U.S. Pat. No. 8393331—IPR2014-02189, Exhibit 1011 Collins Expert Declaration, Aug. 14, 2014.
NJOY, Inc., Petition for Inter Partes Review of U.S. Pat. No. 8490628—IPR2014-01300, Aug. 15, 2014.
NJOY, Inc., Petition for Inter Partes Review of U.S. Pat. No. 8490628—IPR2014-01300, Exhibit 1040—Collins Expert Declaration, Aug. 15, 2014.
NJOY, Inc. et al, Petition for Inter Partes Review of U.S. Pat. No. 8893726—IPR2015-01302, May 29, 2015.
NJOY, Inc. et al., Petition for Inter Partes Review of U.S. Pat. No. 8893726—IPR2015-01302, Exhibit 1002—Nayfeh Expert Declaration, May 29, 2015.
Patent Trial and Appeal Board, United States Patent and Trademark Office, Inter Partes Review Institution Decision IPR2014-01289.
Patent Trial and Appeal Board, United States Patent and Trademark Office, Inter Partes Review Institution Decision IPR2014-01300.
Sottera, Inc., CV11-0367 Invalidity Contentions, Apr. 12, 2012.
Sottera, Inc., Invalidity Contentions, Exhibit 7, CV11-0367, Apr. 12, 2012.
Sottera, Inc., Invalidity Contentions, Exhibit 8, CV11-0367, Apr. 12, 2012.
State Intellectual Property Office, PRC China, Reexamination Decision on the Request for Invalidation for CN200420031182.0, Jun. 22, 2009 with English translation.
State Intellectual Property Office, PRC China, Search Report for PCT/CN2005/000337, Jul. 14, 2005.
United States Patent and Trademark Office Notice of Allowance for U.S. Appl. No. 13/560,789, May 10, 2013.
United States Patent and Trademark Office, Final Office Action for U.S. Appl. No. 12/944,123, Oct. 30, 2012.
United States Patent and Trademark Office, Final Office Action for U.S. Appl. No. 13/777,927, Jan. 16, 2014.
United States Patent and Trademark Office, Non-Final Office Action for U.S. Appl. No. 10/587,707, Sep. 1, 2009.
United States Patent and Trademark Office, Non-Final Office Action for U.S. Appl. No. 12/944,123, Dec. 13, 2011.
United States Patent and Trademark Office, Office Action for U.S. Appl. No. 13/777,927, Aug. 16, 2013.
U.S. District Court, Central District of California, Western Division, Defendant NJOY, Inc.'s Memorandum of Points and Authorities in Support of Defendants' Motion for Leave to Amend Invalidity Contentions dated Jun. 29, 2015 and tiled in Consolidated Case No. CV 14-01645 GW (MRW) and related consolidated cases.
U.S. District Court, Central District of California, Western Division, Defendant NJOY, Inc.'s Declaration of Brent K. Yamashita in Support of Defendants' Motion for Leave to Amend Invalidity Contentions dated Jun. 29, 2015 and filed in Consolidated Case No. CV 14-01645 GW (MRW) and related consolidated cases.
U.S. District Court, Central District of California, Western Division, Defendant Njoy, Inc.'s Exhibit 1 to Defendants' Motion for Leave to Amend Invalidity Contentions dated Jun. 29, 2015 and filed in Consolidated Case No. Cv 14-01645 GW (MRW) and related consolidated cases.
U.S. District Court, Central District of California, Western Division, Defendant NJOY, Inc.'s Exhibit 2 to Defendants' Motion for Leave to Amend Invalidity Contentions dated Jun. 29, 2015 and filed in Consolidated Case No. CV 14-01645 GW (MRW) and related consolidated cases.
U.S. District Court, Central District of California, Western Division, Defendant NJOY, Inc.'s Exhibit 3 to Defendants' Motion for Leave to Amend Invalidity Contentions dated Jun. 29, 2015 and filed in Consolidated Case No. CV 14-01645 GW (MRW) and related consolidated cases.
U.S. District Court, Central District of California, Western Division, Defendant NJOY, Inc.'s Exhibit 4 to Defendants' Motion for Leave to Amend Invalidity Contentions dated Jun. 29, 2015 and filed in Consolidated Case No. CV 14-01645 GW (MRW) and related consolidated cases.
U.S. District Court, Central District of California, Western Division, Defendant NJOY, Inc.'s Exhibit 5 to Defendants' Motion for Leave to Amend Invalidity Contentions dated Jun. 29, 2015 and filed in Consolidated Case No. CV 14-01645 GW (MRW) and related consolidated cases.
U.S. District Court, Central District of California, Western Division, Defendant NJOY, Inc.'s Reply Brief in Support of Defendants' Motion for Leave to Amend Invalidity Contentions dated Jul. 13, 2015 and filed in consolidated Case No. CV 14-01645 GW (MRW) and related consolidated cases.
U.S. District Court, Central District of California, Western Division, Defendant NJOY, Inc.'s production documents VLACHOS 0000061-72; Consolidated Case No. CV 14-01645 GW (MRW) and related consolidated cases.

* cited by examiner

ELECTRONIC CIGARETTE

CROSS REFERENCE TO RELATED APPLICATIONS

This application is a Continuation of U.S. patent application Ser. No. 14/525,066, filed Oct. 27, 2014, and now pending, which is a Continuation of U.S. patent application Ser. No. 13/777,927, filed Feb. 26, 2013, now U.S. Pat. No. 8,893,726, which is a Divisional of U.S. patent application Ser. No. 13/560,789, filed Jul. 27, 2012 and now U.S. Pat. No. 8,490,628, which is a Continuation of U.S. patent application Ser. No. 12/944,123, filed Nov. 11, 2010 and now U.S. Pat. No. 8,393,331, which is a Continuation of U.S. patent application Ser. No. 10/587,707, filed Mar. 9, 2007, now U.S. Pat. No. 7,832,410B2 which claims the benefit of International PCT Application No. PCT/CN05/00337, filed Mar. 18, 2005, which claims the benefit of Chinese Patent Application No. 20040031182.0, filed Apr. 14, 2004, all of which are incorporated herein by reference in their entirety.

TECHNICAL FIELD

The present invention relates to an electronic cigarette, in particular to an electronic atomization cigarette that contains only nicotine without tar.

BACKGROUND ART

Although it is commonly known that "smoking is harmful to your health", the number of smokers worldwide is up to 1 billion, and the number is increasing every year. According to the statistical data from the World Health Organization, about 4.9 million people die of smoking diseases each year. Although smoking may cause serious respiratory diseases and cancer, it remains extremely difficult for smokers to quit smoking completely.

The active ingredient in a cigarette is nicotine. During smoking, nicotine, along with tar aerosol droplets, enter the smoker's alveolus and are rapidly absorbed. The nicotine then affects the receptors of the smoker's central nervous system.

Nicotine is a kind of alkaloid with low molecular weight. A small dose of nicotine is essentially harmless to human body and its half-life in blood is quite short. The major harmful substance in tobacco is tar. Tar in tobacco is composed of thousands of ingredients. Several of these are cancerogenic.

Some cigarette substitutes that contain only nicotine without tar have been proposed. Many of them, such as "nicotine patch", "nicotine mouthwash", "nicotine chewing gum", "nicotine drink" etc., are made of pure nicotine. Although these cigarette substitutes are free from tar, their major disadvantage is that an effective peak concentration cannot be reached in the blood of a smoker due to slow absorption of nicotine In addition, these cigarette substitutes cannot satisfy habitual smoking actions of a smoker, for example, inhaling action, and thus are not likely to be widely accepted as effective substitutes for smoking.

THE SUMMARY OF THE INVENTION

An electronic atomization cigarette that functions as substitutes for quitting smoking and cigarette substitutes includes a shell; a mouthpiece; an air inlet provided in the external wall of the shell; an electronic circuit board, a sensor, an atomizer, and a liquid-supply within the shell. A stream passage is provided on one side of the sensor. An atomization cavity is arranged in the atomizer. The liquid-supply is in contact with the atomizer.

DETAILED DESCRIPTION

Embodiment 1

Figure 1:
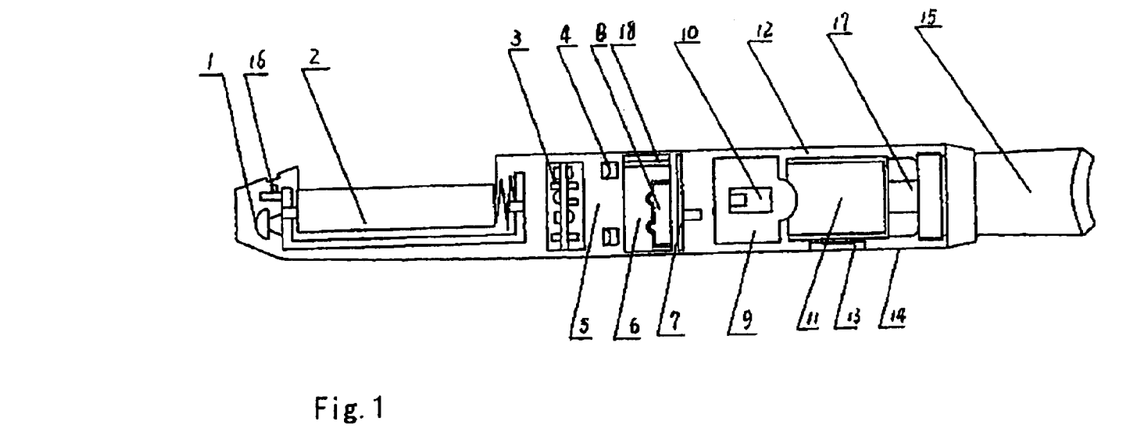
FIG. 1 is a schematic diagram of an overall structure.

As shown in FIG. 1, an air inlet 4 is provided on the external wall of the shell 14. A LED 1, a cell 2, an electronic circuit board 3, a normal pressure cavity 5, a sensor 6, a vapor-liquid separator 7, an atomizer 9, a liquid-supplying bottle 11 and a mouthpiece 15 are sequentially provided within the shell 14. The electronic circuit board 3 comprises an electronic switching circuit and a high frequency generator.

Figure 4:
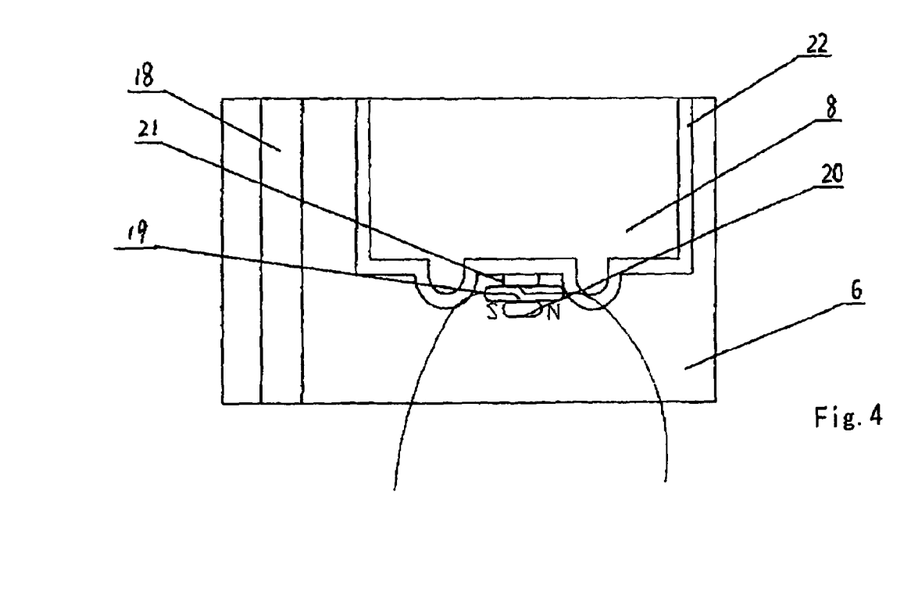
FIG. 4 is a structural diagram of a sensor.

As shown in FIG. 4, a negative pressure cavity 8 is provided in the sensor 6 and is separated from the sensor 6 by a film 22 A first magnetic steel 20, a second magnetic steel 21 and a Reed switch 19 arranged between them is also provided within the sensor 6. The second magnetic steel 21 is attached to the film 22. The atomizer 9 is in contact with the liquid-supplying bottle 11 via the bulge 36, and the atomization cavity 10 is provided in the atomizer 9.

Figure 6:
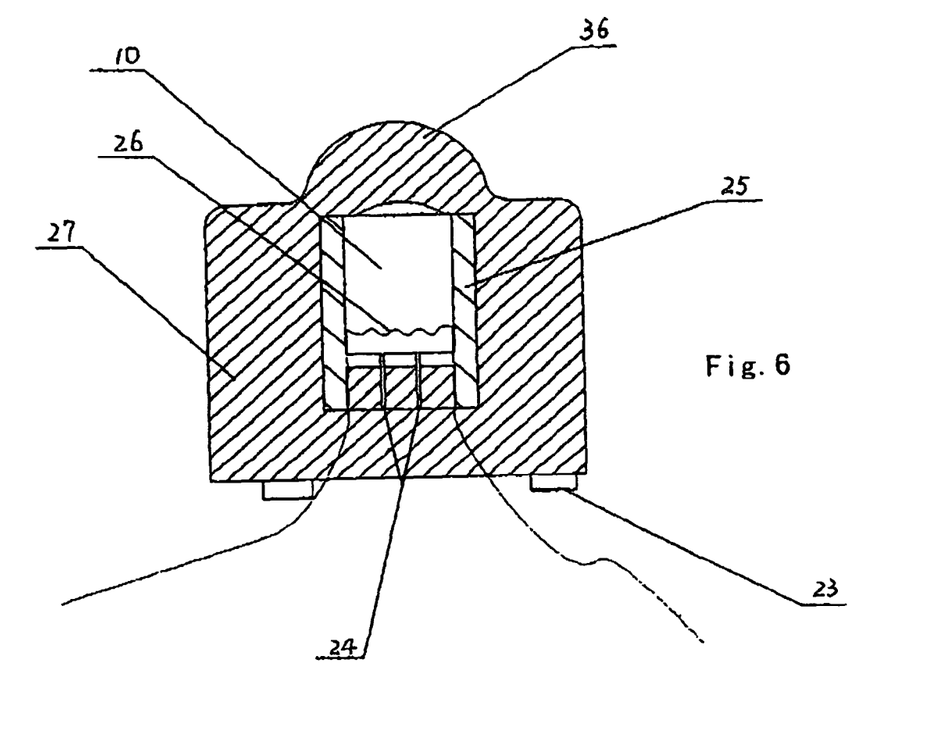
FIG. 6 is a structural diagram of an atomizer.
Figure 7:
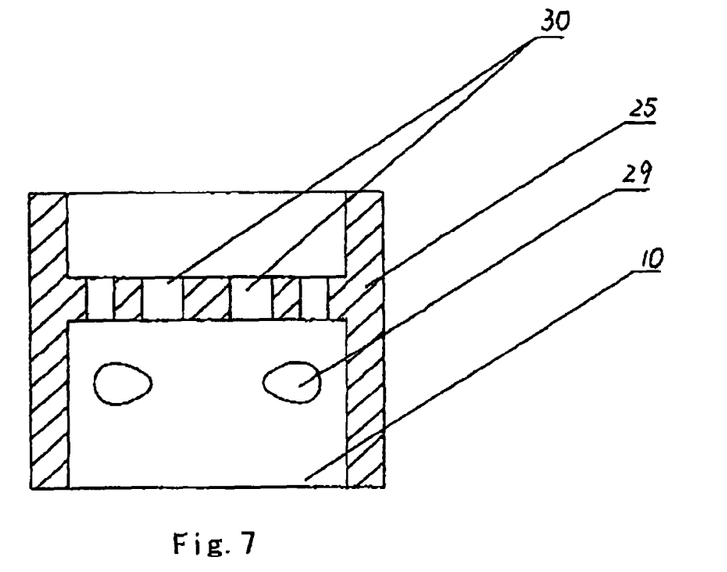
FIG. 7 is a structural diagram of the ceramic member in an atomizer.

As shown in FIGS. 6 and 7, the overflow hole 29 is provided on the wall 25 of the atomization cavity 10. A heating element 26, which can be made of platinum wire, nickel chromium alloy or iron chromium aluminum alloy wire with rare earth element, is provided within the cavity, and can also be made into a sheet form with conductive ceramics or PTC ceramics. An ejection hole is provided on the side opposite to the heating element 26. The ejection hole can be determined to select either the long stream ejection hole 24 or the short stream ejection hole 30, depending on the material used for the atomization cavity wall 25. The long stream ejection hole 24 can employ slot structure of 0.1 mm-1.3 mm or circular hole structure with a single and multiple holes. The short stream ejection hole 30 has the diameter of about 0.3 mm-1.3 mm.

Figure 2:
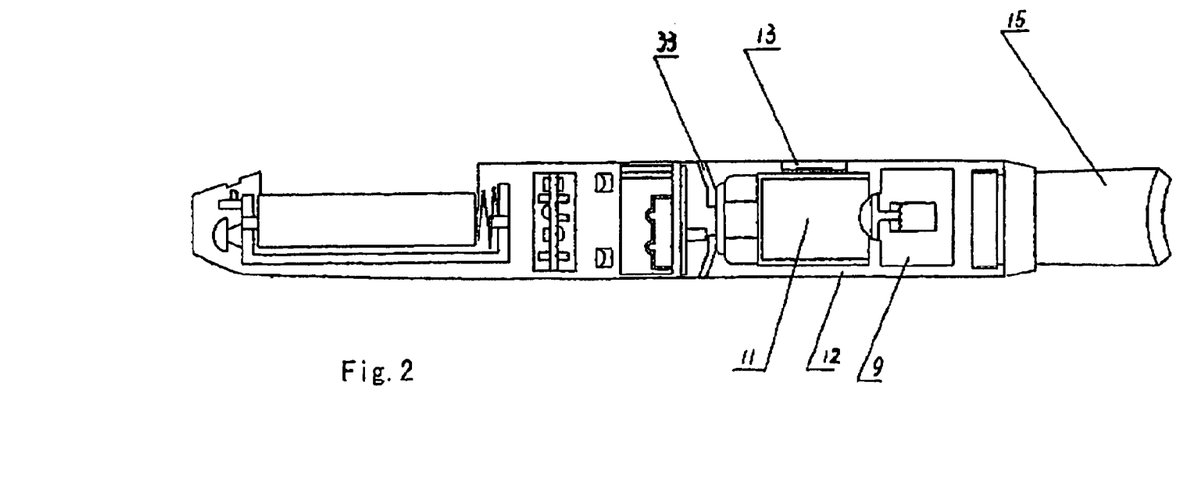
FIG. 2 is a schematic diagram of another overall structure.
Figure 9:
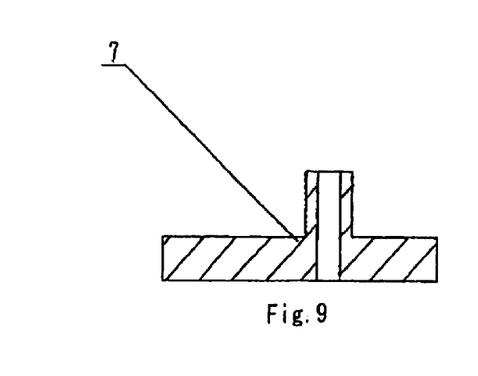
FIG. 9 is a structural diagram of a vapor-liquid separator.

The atomization cavity wall 25 is surrounded with the porous body 27, which can be made of foam nickel, stainless steel fiber felt, high molecule polymer foam and foam ceramic. A first piezoelectric element 23 is also provided on the atomizer 9. The atomization cavity wall 25 can be made of aluminum oxide or ceramic. As shown in FIG. 9, a through hole is provided on the vapor-liquid separator 7, and can be made of plastic or silicon rubber. As shown in FIG. 2, a retaining ring 13 for locking the liquid-supplying bottle 11 is provided between one side of the liquid-supplying bottle 11 and the shell 14. An aerosol passage 12 is provided on the other side of the liquid-supplying bottle.

Figure 11:
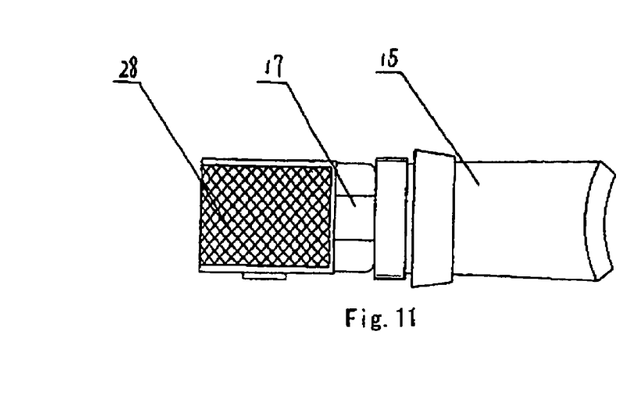
FIG. 11 is a structural diagram of the connection of a liquid-supplying bottle and a mouthpiece.

As shown in FIG. 11, the solution storage porous body 28 is provided in the liquid-supplying bottle, and can be filled with polypropylene fiber, terylene fiber or nylon fiber, or be filled with plastic shaped by foaming, such as polyamine resin foam column or polypropylene foam column. Alternatively, it may be made of a column formed by molding polyvinyl chloride, polypropylene, polycarbonate into a stack of laminated layers. The air inlet 4, normal pressure cavity 5, vapor-liquid separator 7, atomizer 9, aerosol passage 12, gas vent 17, mouthpiece 15 are sequentially interconnected.

Figure 12:
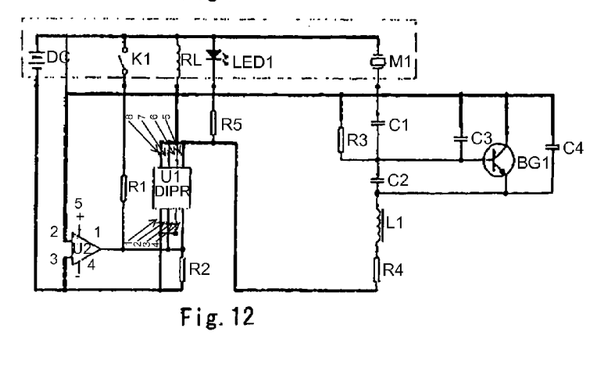
FIG. 12 is a functional diagram of a circuit.

As shown in the functional diagram of the circuit in FIG. 12, K1 refers to the Reed switch 19, RL refers to the heating element 26, LED1 refers to the Light Emitting Diode 1, U2 refers to the low voltage detecting element used for the overdischarging protection of the lithium cell, M1 refers to the first piezoelectric element 23, and C1, C2, R3, L1, C3, BG, M1 collectively constitute a Colpitts oscillator. The operating principle of the circuit is as follows: when K1 is closed, U1, i.e., the field effect power transistor, is turned on, RL starts, and the Colpitts oscillator starts oscillating, M1 will provide the high frequency mechanical oscillatory wave to the atomizer 9.

When a smoker smokes, the mouthpiece 15 is under negative pressure. The air pressure difference or high speed stream between the normal pressure cavity 5 and the negative pressure cavity 8 causes the sensor 6 to output an actuating signal, the electronic circuit board 3 connected therewith goes into operation. Now the ripple film 22 in the sensor 6 is deformed to take the second magnetic steel 21 away from the Reed switch 19. The Reed switch 19 is then closed (i.e., K1 is closed) under the effect of the excessive magnetic line of force from the first magnetic steel 20, starting the field effect power transistor electronic switch (i.e., U1 is opened). The high frequency oscillator may uses the Colpitts oscillator with the frequency of 550 KHz-8 MHz. The automatic fine-adjusting element in the circuit resonates with the first piezoelectric element 23. The LED 1 can be lit under the supply of the rechargeable battery 2.

Air enters the normal pressure cavity 5 through the air inlet 4, passes through the air passage 18 of the sensor and then the through hole in the vapor-liquid separator 7, and flows into the atomization cavity 10 in the atomizer 9. The high speed stream passing through the ejection hole drives the nicotine solution in the porous body 27 to eject into the atomization cavity 10 in the form of droplets, where the nicotine solution is subjected to the ultrasonic atomization by the first piezoelectric element 23 and is further atomized by the heating element 26.

After the atomization the droplets with large diameters stick to the wall under the action of eddy flow and are reabsorbed by the porous body 27 via the overflow hole 29. Droplets with small diameters float in stream and form aerosols, which are sucked out via the aerosol passage 12, gas vent 17 and mouthpiece 15. The solution storage porous body 28 in the liquid-supplying bottle 11 is in contact with the bulge 36 on the atomizer 9, thereby achieving the capillary infiltration liquid-supplying.

The mouthpiece 15 is threaded. When the nicotine solution in the liquid-supplying bottle 11 is used up, users can screw the mouthpiece 15 out to take the liquid-supplying bottle 11 out, refill the liquid-supplying bottle 11 with the nicotine solution, put the liquid-supplying bottle 11 into the shell 14 again, and then screw the mouthpiece 15.

The Reed switch 19, the first magnetic steel 20, the second magnetic steel 21, the ripple film 22 can be replaced by a semiconductor strain gauge with sealed film, which is mounted in the place of the sensor ripple film.

Figure 8:
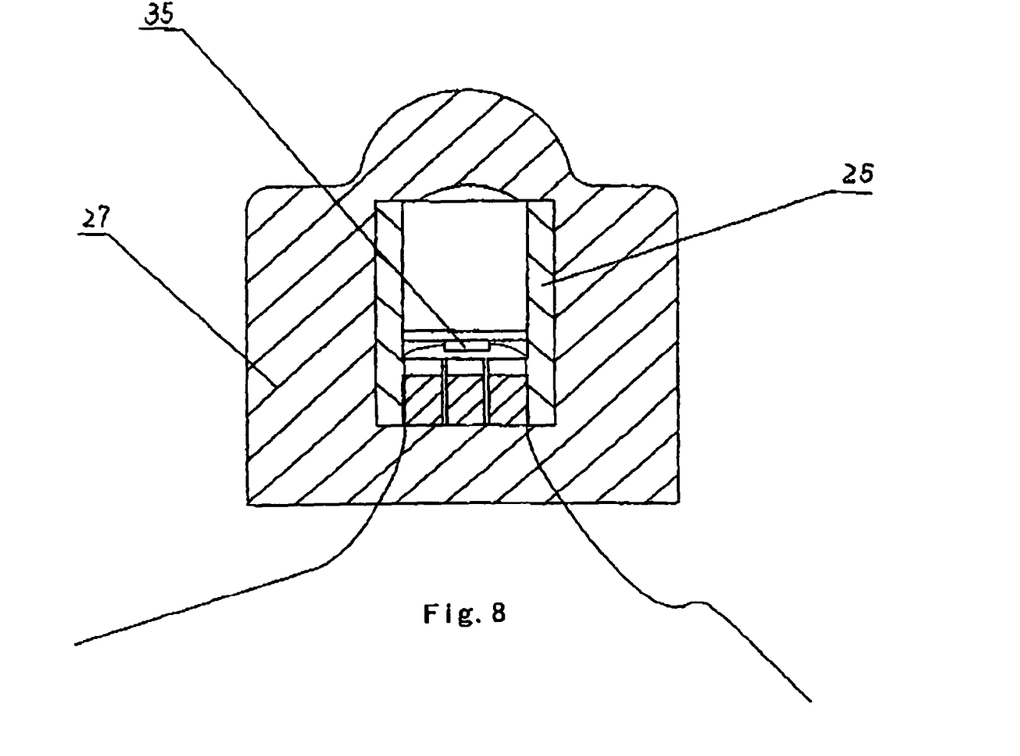
FIG. 8 is a structural diagram of another atomizer.

To simplify the design, the first piezoelectric element 23 on the atomizer 9 can be omitted, and the atomization of the nicotine solution will be made only by the heating element 26. The size of such an atomizer can be made smaller, and the structure of the connection of the whole electronic atomization cigarette is the same as the embodiment 1. In addition, as shown FIG. 8, the first piezoelectric element 23 and the heating element 26 in the atomizer 9 can be omitted, an additional second piezoelectric element 35 in the form of platen with a single layer or multiple laminated layers can be arranged in the atomization cavity, and the stream passing through the ejection hole vibrates the focus at the center of the second piezoelectric element 35 to achieve the effect of strong ultrasonic atomization.

Figure 10:
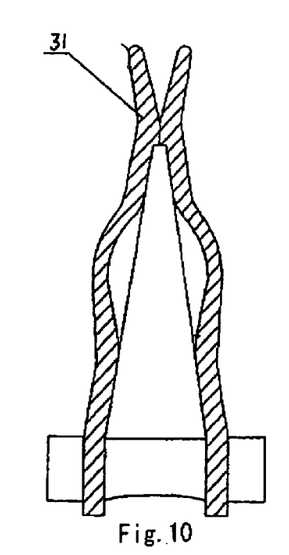
FIG. 10 is a structural diagram of another vapor-liquid separator.

As shown in FIG. 10, a silicon gel check valve 31 may cover the outside of the through hole on the vapor-liquid separator 7. During smoking, a stream reaches the through hole, as the air pressure in the through hole increases, the silicon gel check valve 31 is opened and the stream passes; otherwise, the silicon gel check valve 31 is closed.

Figure 5:
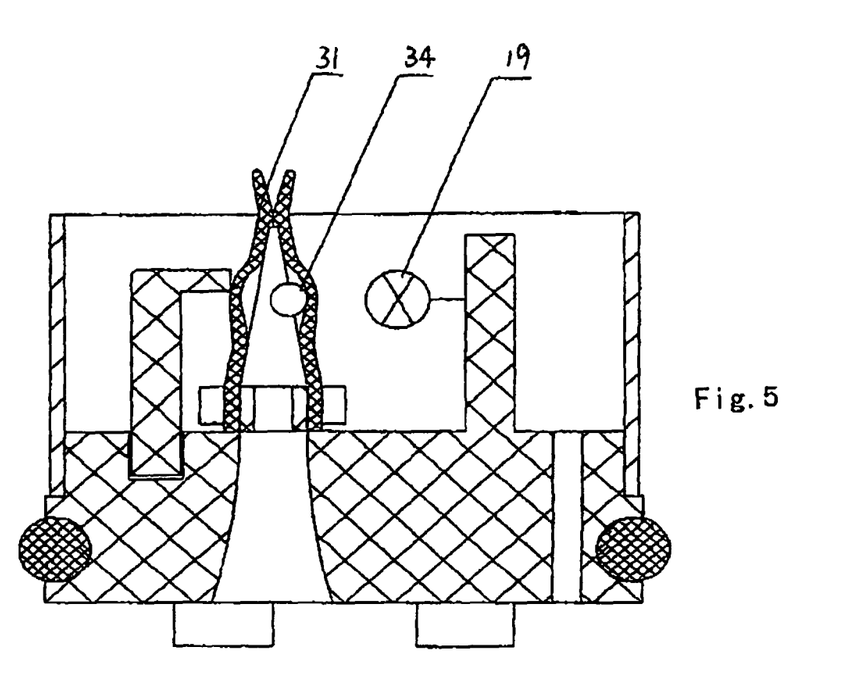
FIG. 5 is a structural diagram of a sensor with a silicon gel check valve.

As shown in FIG. 5, the sensor 6 may also be designed into a structure with the silicon gel check valve 31. During smoking, the stream comes into the silicon gel check valve 31, the air pressure increases and the air expands, the third magnetic steel 34 in the valve approaches the Reed switch 19 gradually until the Reed switch is closed and the circuit is turned on, and the air outlet of the silicon gel check valve 31 is opened with the increment of the air pressure difference. The Reed switch 19 can also be made of Hall device or magneto diode or magneto triode instead.

Embodiment 2

As shown in FIG. 2, to improve the liquid-supplying state, the liquid-supplying bottle 11 is arranged between the vapor-liquid separator 7 and the atomizer 9. A spring piece 33 for pressing the liquid-supplying bottle 11 on the atomizer 9 is provided on one end of the liquid-supplying bottle 11. Other components and their functions are the same as those in the embodiment 1.

Figure 3:
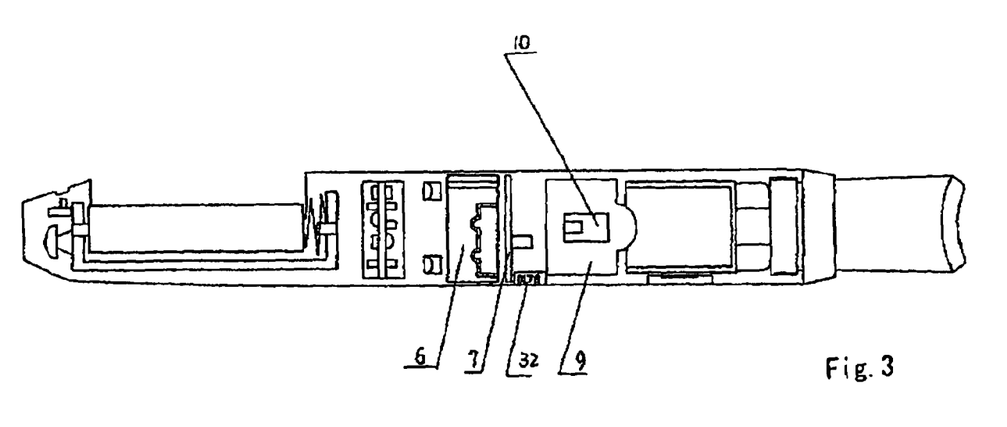
FIG. 3 is a schematic diagram of an overall structure with a display screen.

On the inner wall of the shell 14 of the electronic atomization cigarette described in the embodiment 1 and 2, a digital display screen 32 for showing the smoking times per day and the cell capacity can be also provided. The sensor 6 uses a linear signal output, which is proportional to the suction force (i.e., the stronger one sucks, the longer the time of operation is), the atomizer 9 operates in the linear mode, thereby simulating a cigarette that looks like a normal cigarette.

Within the shell 14, the microswitch 16 is connected to the sensor 6 in parallel and used for manually cleaning. When users do not smoke, they press the microswitch 16 to start the sensor 6 connected therewith in parallel, or clean the residue or other impurity substance within the shell 14.

The nicotine solution for atomization contains 0.4-3.5% nicotine, 0.05-2% cigarette essence, 0.1-3.1% organic acid, 0.1-0.5% anti-oxidation agent, and the rest is 1,2-propylene glycol.

The invention claimed is:
1. An electronic vaporizing device comprising:
a cylindrical housing having a longitudinal axis, a first end and a second end;
an LED at a first end of the cylindrical housing to simulate a cigarette;

an outlet at the second end of the cylindrical housing;
an air inlet for allowing air to flow into the cylindrical housing;
a battery, an electronic circuit board, a sensor, an atomizer comprising a hollow cylindrical chamber and a heating wire, and a liquid-supply within the cylindrical housing;
the hollow cylindrical chamber co-axial with the cylindrical housing;
the heating wire extending across the cylindrical chamber perpendicular to the longitudinal axis of the cylindrical housing;
an air stream passage between the inlet and the outlet, with the air stream passage leading to the atomizer to allow air to pass through the atomizer and across the heating wire;
with the liquid-supply in physical contact with the atomizer; and
wherein the liquid-supply is cylindrical and parallel to the longitudinal axis of the cylindrical housing.

2. The device of claim 1 with the liquid-supply comprising a fiber material.

3. The device of claim 2 with the liquid-supply comprising propylene glycol.

4. The device of claim 3 further including a separator in the cylindrical housing, with the electronic circuit board and the sensor on a first side of the separator, and with the atomizer and the liquid-supply on a second side of the separator, opposite from the first side.

5. The device of claim 4 with the separator having a through hole from the first side to the second side, and with the separator comprising plastic or rubber.

6. The device of claim 1 wherein the sensor creates an output signal which is proportional to suction force on the outlet.

7. The device of claim 6 wherein the electronic circuit board provides electric current to the heating wire for a time interval dependent on the suction force sensed by the sensor.

8. The device of claim 6 wherein illumination of the LED is dependent on the suction force sensed by the sensor, to simulate an appearance of a cigarette.

9. The device of claim 6 wherein the sensor comprises a pressure sensor.

10. The device of claim 6 further including a switch electrically connected to the sensor, to operate the heating wire without suction on the outlet, for manually cleaning within the cylindrical housing.

11. The device of claim 1 with the battery, the liquid-supply and the cylindrical chamber of the atomizer co-axial with the longitudinal axis of the cylindrical housing.

12. An electronic vaporizing device comprising:
a cylindrical housing having a longitudinal axis, a first end and a second end;
an LED at a first end of the cylindrical housing;
an outlet at the second end of the cylindrical housing;
an air inlet for allowing air to flow into the cylindrical housing;
a battery, an electronic circuit board, a sensor, an atomizer, and a liquid-supply within the cylindrical housing, wherein the liquid-supply includes a liquid and a fiber material, with the liquid containing propylene glycol, and wherein the liquid supply is cylindrical and parallel to the longitudinal axis of the cylindrical housing;
the atomizer comprises a porous component, a hollow cylindrical chamber and a heating wire;
the porous component is in physical contact with the liquid in the liquid supply;
the hollow cylindrical chamber is co-axial with the cylindrical housing;
the heating wire extending across the cylindrical chamber of the atomizer perpendicular to the longitudinal axis of the cylindrical housing; and
an air stream passage from the inlet through the cylindrical chamber of the atomizer to the outlet, and the heating wire positioned in the air stream passage.

13. The device of claim 12 further comprising a separator in the cylindrical housing, with the electronic circuit board and the sensor on a first side of the separator, and with the atomizer and the liquid-supply on a second side of the separator, opposite from the first side, and with the separator having a through hole from the first side to the second side.

14. The device of claim 12 wherein the sensor creates an output signal which is proportional to suction force on the outlet.

15. The device of claim 14 wherein the electronic circuit board provides electric current to the heating wire for a time interval dependent on the suction force sensed by the sensor.

16. The device of claim 15 wherein illumination of LED is dependent on the suction force sensed by the sensor, to simulate an appearance of a cigarette.

17. An electronic vaporizing device comprising:
a cylindrical housing having a longitudinal axis, a first end and a second end;
an LED at the first end of the cylindrical housing;
an outlet at the second end of the cylindrical housing;
an air inlet for allowing air to flow into the cylindrical housing;
a battery, an electronic circuit board, a sensor, a porous component, and a liquid-supply within the cylindrical housing;
a heating wire positioned perpendicular to the longitudinal axis of the cylindrical housing;
an air passage between the inlet to the outlet, with the heating wire in the air passage and positioned for air to flow over the heating wire;
with the liquid-supply in physical contact with the porous component, to move liquid from the liquid-supply to the porous component; and
wherein the liquid-supply is cylindrical and arranged parallel to the longitudinal axis of the cylindrical housing.

18. The device of claim 17 with the porous component comprising a fiber material.

19. The device of claim 18 with the battery and the liquid-supply co-axial with the longitudinal axis of the cylindrical housing.

20. The device of claim 18 with at least one end of the porous component projecting into the liquid-supply.

21. The device of claim 18 with the liquid-supply comprising propylene glycol.

22. The device of claim 18 wherein the sensor creates an output signal which is proportional to suction force on the outlet.

23. The device of claim 18 wherein illumination of LED is dependent on the suction force sensed by the sensor, to simulate an appearance of a cigarette.

24. The device of claim 18 further including a switch electrically connected to the sensor, to operate the heating wire without suction on the outlet, for manually cleaning within the cylindrical housing.

25. The device of claim 20 further including a separator in the cylindrical housing, with the electronic circuit board, and the sensor on a first side of the separator, and with the porous component and the liquid-supply on a second side of the separator, opposite from the first side.

26. The device of claim 25 with the separator having a through hole from the first side to the second side.

27. The device of claim 25 wherein the heating wire has leads extending out of the porous component.

* * * * *